United States Patent [19]

Aichinger et al.

[11] Patent Number: 4,550,419
[45] Date of Patent: Oct. 29, 1985

[54] DIAGNOSTIC RADIOLOGY SETUP WITH MEANS FOR SUPPRESSING STRAY RADIATION

[75] Inventors: Horst Aichinger, Fuerth; Paul Marhoff; Manfred Pfeiler, both of Erlangen, all of Fed. Rep. of Germany

[73] Assignee: Siemens Aktiengesellschaft, Berlin and Munich, Fed. Rep. of Germany

[21] Appl. No.: 543,208

[22] Filed: Oct. 19, 1983

[30] Foreign Application Priority Data

Feb. 8, 1983 [DE] Fed. Rep. of Germany ....... 3304213

[51] Int. Cl.$^4$ .......................... A61B 6/00; H04N 5/32
[52] U.S. Cl. ..................................... 378/099; 358/111
[58] Field of Search ................... 378/7, 2, 87, 99, 154; 358/111

[56] References Cited

U.S. PATENT DOCUMENTS 4,087,837  5/1978  Geluk .................................... 378/99

FOREIGN PATENT DOCUMENTS 2452166  5/1976  Fed. Rep. of Germany ...... 378/154

Primary Examiner—Alfred E. Smith
Assistant Examiner—T. N. Grigsby
Attorney, Agent, or Firm—John Francis Moran

[57] ABSTRACT

The invention relates to a diagnostic radiology setup with means for suppressing stray radiation and with an image intensifier television chain with image storing means. There is provided a perforated diaphragm of radiation-absorbing material near the tube, which diaphragm can be introduced into the ray path selectively. Two image memories for an X-ray picture with a diaphragm and an X-ray picture without a diaphragm and an image processing system serve for comparing the image information of the two X-ray pictures to determine and eliminate the stray radiation component.

7 Claims, 2 Drawing Figures

DIAGNOSTIC RADIOLOGY SETUP WITH MEANS FOR SUPPRESSING STRAY RADIATION

BACKGROUND OF THE INVENTION

The invention relates to a diagnostic radiology setup with means for suppressing stray radiation and with an image intensifier television chain with image storing means.

The stray radiation produced in an object during an X-ray examination not only reduces the contrast obtained through the primary radiation but it also affects, for example, the precision of the image subtraction methods used in angiography. In such methods, an image taken of a region of a patient without a contrast medium is subtracted from an image with a contrast medium of the same region.

To reduce this undesirable effect and to eliminate, to a large extent, the stray radiation it is a known practice to move over the X-ray film a slit diaphragm situated near the film, and to produce the X-ray picture line by line. The slit diaphragm shields the film from stray radiation to a substantial extent (German Patent Application P 31 38 939.2). With computer tomographs it is known and possible to produce an X-ray shadow picture by means of a relative movement between a patient table and a line type X-ray detector. This is described in German Patent Application DE-OS 26 13 809. Both possibilities have the disadvantage, however, that the composition time—that is the time to process a complete picture—is relatively long.

SUMMARY OF THE INVENTION

It is an object of the present invention to provide a diagnostic radiology setup of the above mentioned type with the additional feature that an image which is primarily free from stray radiation components is produced in a short time without exposing the patient to any major additional radiation.

This object is achieved according to the invention by a perforated diaphragm of radiation-absorbing material which is insertable near the tube, which diaphragm can be selectively introduced into the ray path; two image storing devices for storing an X-ray picture with and an X-ray picture without the perforated diaphragm; and an image processing system for comparing the image information of the two X-ray pictures to determine and eliminate stray radiation components. In the diagnostic radiology setup according to the invention it is possible, through subtraction of the contents of the two image storing devices, to determine the local stray radiation component and to produce (by subtraction of this stray radiation component from the X-ray pictures of the actual radiological process) X-ray pictures with a low content of stray radiation.

Other features and advantages of the invention will be apparent from the following description of the preferred embodiments, and from the claims.

For a full understanding of the present invention, reference should now be made to the following detailed description of the preferred embodiments of the invention and to the accompanying drawings.

DETAILED DESCRIPTION

Figure 1:
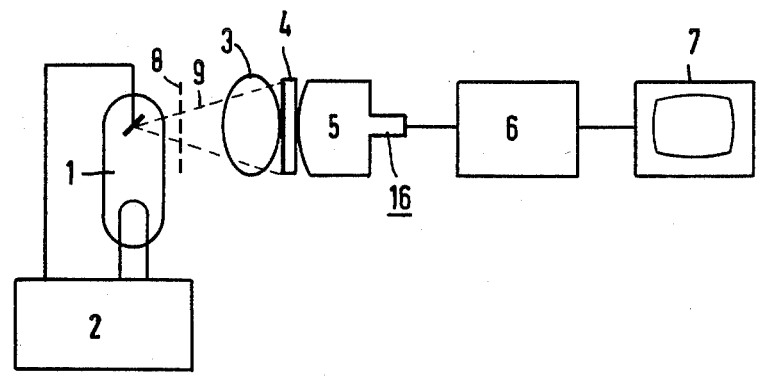
FIG. 1 shows a diagnostic radiology setup according to the invention.

In FIG. 1, an X-ray tube 1 is shown, which is powered by an X-ray generator 2. The X-ray radiation pass through a patient 3, and produce on an input fluorescent screen of an image intensifier 5 X-ray shadow pictures. The pictures are received by a television camera 16 and are presented to a viewer 7 via an image processing system 6. Between the X-ray tube 1 and the patient 3, nearer to the tube 1, is located a diaphragm 8 of radiation-absorbing material with a plurality of holes which can be selectively introduced into the ray path 9.

Figure 2:
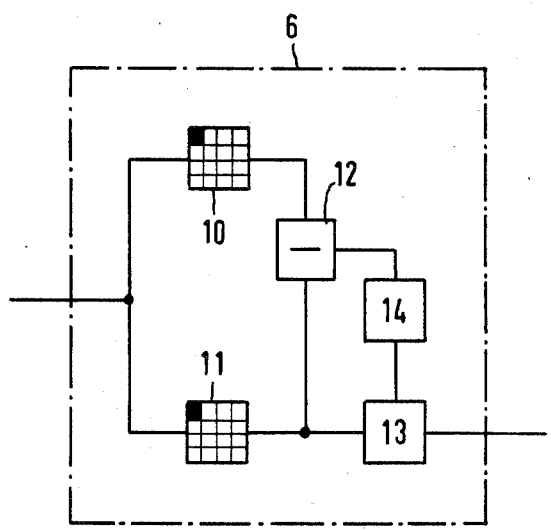
FIG. 2 shows a detail of the diagnostic radiology setup according to FIG. 1.

The image processing system 6 contains, according to FIG. 2, an image memory 10 of relatively low capacity and an image memory 11. The outputs of the image memories 10 and 11 are connected to a subtraction stage 12, the output signal of which is supplied via a control stage 13 to the viewer 7.

To take an X-ray picture, the patient 3 is first irradiated while the diaphragm 8 is in the ray path 9. The X-ray picture thus produced is stored in the smaller memory 10. Thereafter, the diaphragm 8 is removed from the ray path 9 and a second X-ray picture is taken and stored in the memory 11. During the first irradiation with diaphragm 8, the holes thereof allow radiation to go through and pass through the patient 3 and impinge on the input fluorescent screen of the image intensifier 5. With sufficient spacing of the openings of diaphragm 8 and hence of the picture elements, it may be assumed that the signal produced for each picture element is a primary radiation signal which is practically free of stray radiation components. The stray radiation to be taken into consideration and subtracted from the actual X-ray picture, produced without diaphragm 8, is determined as follows. By using the picture elements corresponding to radioscopy with diaphragm 8, a signal difference is generated representing the difference between an X-ray picture with and an X-ray picture without the diaphragm 8. This is accomplished through subtraction stage 12. The mixer stage 13 is thus able to supply to the viewer 7 a video signal which is largely free of stray radiation components. That is, one subtracts from the respective real video signals the corresponding stray radiation signals. The next signal is the output signal of the subtraction stage 12. The net signal represents one component in the matrix of the real total picture. That component is interpolated in the interpolation stage 14.

The patient 3 is exposed to a minimal additional radiation due to the radiation passing through the openings in the perforated diaphragm 8. Because of the arrangement of the diaphragm in proximity to the tube, the dimensions of the diaphragm are relatively small which allows easy mechanical handling and manipulation of the diaphragm.

To ensure comparability between trial pictures with the diaphragm 8 and an actual picture without the diaphragm 8, means for determining the X-ray dosage of the two pictures may be provided in a preferred embodiment. The requirements for mechanical precision can be lowered if means are present for locating the signal in the center of the picture element of a trial picture with diaghragm 8.

In the case of the embodiment described above, the stray radiation is at first determined only for those picture elements which are established by the holes of the perforated diaphragm 8. Through the above mentioned interpolation it is possible to determine the stray radiation over the entire X-ray picture.

In a variant of the diagnostic radiology setup described above, instead of a perforated diaphragm with a plurality of holes a slit diaphragm located close to the tube is provided, as described in German Patent Application P 31 38 939.2. This slit diaphragm can be introduced into the ray path for generating a trial picture and can then be moved in such a way that the patient 3 is scanned by a fan-shaped X-ray beam over the region to be examined. In this case, accordingly, there is produced on the input screen of the image intensifier 5 a line-by-line image which scans the input screen. In accordance with the movement of this line type image, electronic scanning of the X-ray picture can in this case be effected in the television chain 5, 6, 7, and 16, so that only the video signal which corresponds to the line type picture is transmitted to the image storing device 10. The dosage rate can be kept low if the width of the line type image and the width of the input screen are adapted to the scanning. This means, for example, that with an image intensifier with a 25-cm input screen and a width of 1 cm of the line type image, at e.g. 40 ms for an image scanning period, a time of 25×40 ms=1 sec is obtained for the total process. This corresponds to the same generator power needed for the production of an image without a slit diaphragm. Slit process times can be selected analogously for other image scanning periods of e.g. 20 ms, 80 ms, 320 ms or corresponding times at a line frequency of 60 Hz.

If the image intensifier television chain 5, 6, 7, and 16 is equipped with a dosage rate control, the comparability of a trial picture and the picture without diaphragm can be ensured by switching the amplifier of the dosage rate control according to the difference between the generator power of the trial picture and the picture without diaphragm. During the trial take, dosage rate control does not take place.

In another embodiment pictures for comparison are obtained with an image intensifier television chain where the data for picture-taking are derived from radioscopic data. That is, a picture in accordance with the respective patient transparence and dosage rate control settings during normal and non trail takes is used. This is accomplished through the following procedure. First the data for taking a picture with a diaphragm, e.g. a multi-hole diaphragm or a slit diaphragm, are automatically set as derived from the radioscopy. In this case dosage rate control is not applicable. Then a survey picture is taken without a diaphragm, but with dosage rate control. From the required readjustment of the generator power as compared with the take with diaphragm one obtains a correction factor for the evaluation of the radiograph.

Finally, in a diagnostic setup with dosage control, it is possible also—in the instance where dosage rate control is effected for the first of a series of pictures—to take survey pictures without a diaphragm with the dosage rate control inserted at least for the first picture and concluding with a picture with a diaphragm. The assumption to be made here is that the data for the last picture complys with the required accuracy of the data of the previous pictures. This procedure ensures correspondence between the trial picture and the pictures without diaphragm, but in this case only off-line operation is possible.

When using a diaphragm with a plurality of holes, the additional exposure of the patient for determining the stray radiation is minimal, because for this purpose the patient is irradiated only with a few thin beams. But as previously described an interpolation is necessary for determination of the stray radiation over the entire picture.

On the other hand, if a slit diaphragm is introduced into the ray path for stray radiation determination, the additional exposure of the patient is equivalent to one take. Interpolation, however, in this case, is not necessary.

There has thus been shown and described novel apparatus for diagnostic radiology which fulfills all the objects and advantages sought therefor. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. A diagnostic radiology set up for suppressing stray radiation components which comprises, in combination:
    (a) an image intensifier television chain, said chain having an image intensifier, a television camera and viewing means for developing and presenting an X-ray picture;
    (b) a tube for generating an X-ray beam;
    (c) a perforated diaphragm of radiation absorbing material capable of being selectively introduced into said X-ray beam;
    (d) first and second image storing means for storing image information for a first X-ray picture generated with said diaphragm and a second X-ray picture generated without said diaphragm; and
    (e) an image processing system for comparing said first and second X-ray pictures so that stray radiation components may be identified and eliminated to generate a stray radiation free X-ray picture.

2. A diagnostic radiology set up as recited in claim 1, further comprising means for sensing and receiving dosage control signals associated with said first and second X-ray pictures.

3. A diagnostic radiology set up according to claim 2, wherein said image intensifier television chain further comprises a dosage rate control, said dosage rate control having an amplifier controllable by and dependent on the difference between the generated power of said first and second X-ray pictures.

4. A diagnostic radiology set up according to claim 2, which further comprises:
    (a) an X-ray dosage control;
    (b) means for storing X-ray data derived from a radioscope of a patient; and
    (c) means for generating a correction signal, said correction signal being dependent on the degree of control required for readjustment of an X-ray picture taken without said diaphgram in comparison with a preceding X-ray picture taken with said diaphragm.

5. The diagnostic radiology set up as recited in claim 1, wherein an X-ray picture with said diaphragm is taken after an X-ray picture without said diaphragm, and wherein said radiology set up includes a dosage rate control.

6. The diagnostic radiology set up according to claims 1, 2, 3, 4 or 5 further comprising means for locating a signal in the center of a picture element of a trial X-ray take.

7. The diagnostic radiology set up according to claims 1 or 2, wherein said first memory for storing data for said first X-ray picture has a smaller capacity than said second memory for storing said second X-ray picture.

* * * * *